United States Patent
Cherwin et al.

[11] Patent Number: 6,124,486
[45] Date of Patent: *Sep. 26, 2000

[54] PROCESS FOR MAKING LOW CALORIE TRIGLYCERIDES HAVING LONG AND SHORT FATTY ACID CHAINS

[75] Inventors: Daniel Eric Cherwin, Penfield, N.Y.; James William Johnson, Jr., Kingsport, Tenn.

[73] Assignee: Eastman Chemical Company, Kingsport, Tenn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/792,617

[22] Filed: Jan. 31, 1997

[51] Int. Cl.$^7$ .................................................. C11C 3/10
[52] U.S. Cl. ............................................... 554/169
[58] Field of Search ............................................ 554/169

[56] References Cited

U.S. PATENT DOCUMENTS

| | | | |
|---|---|---|---|
| 2,615,159 | 10/1952 | Jackson | 260/410.8 |
| 2,962,419 | 11/1960 | Minich | 167/81 |
| 3,579,548 | 5/1971 | Whyte | 260/410.7 |
| 3,600,186 | 8/1971 | Mattson et al. | 99/1 |
| 4,582,715 | 4/1986 | Volpenhein | 426/201 |
| 4,927,658 | 5/1990 | Klemann et al. | 426/611 |
| 4,927,659 | 5/1990 | Klemann et al. | 426/611 |
| 4,959,466 | 9/1990 | White | 536/119 |
| 5,434,278 | 7/1995 | Pelloso et al. | 554/165 |

OTHER PUBLICATIONS

Journal of Food Science, vol. 49 (1984), pp. 419–428, D. Hamm, "Preparation & Evaluation of Trialkoxytricarballylate, Trialkoxycitrate, Trialkoxyglycerylether, Jojoba Oil and Sucrose Polyester as Low Calories Replacements of Edible Fats and Oils".

*Primary Examiner*—Deborah D. Carr
*Attorney, Agent, or Firm*—Quarles & Brady LLP

[57] ABSTRACT

The specification discloses a process for making low calorie triglycerides. The process involves interesterifying short triglycerides having $C_2$ to $C_{10}$ fatty acid chains and long triglycerides having $C_{16}$ to $C_{24}$ fatty acid chains in the presence of a catalyst and without a solvent to produce low calorie triglycerides as an interesterification product of the long and short triglycerides comprising individual triglycerides wherein a substantial is portion of the low calorie triglycerides have two long $C_{16}$ to $C_{24}$ fatty acid chains and one short $C_2$ to $C_{10}$ fatty acid chain having at least one long $C_{16}$ to $C_{24}$ fatty acid chain and at least one short $C_2$ to $C_{10}$ fatty acid chain. The process enables continuous production of low calorie triglycerides with recycle of catalyst and unreacted starting materials for an economical mode of operation with improved product yield and quality.

22 Claims, 1 Drawing Sheet

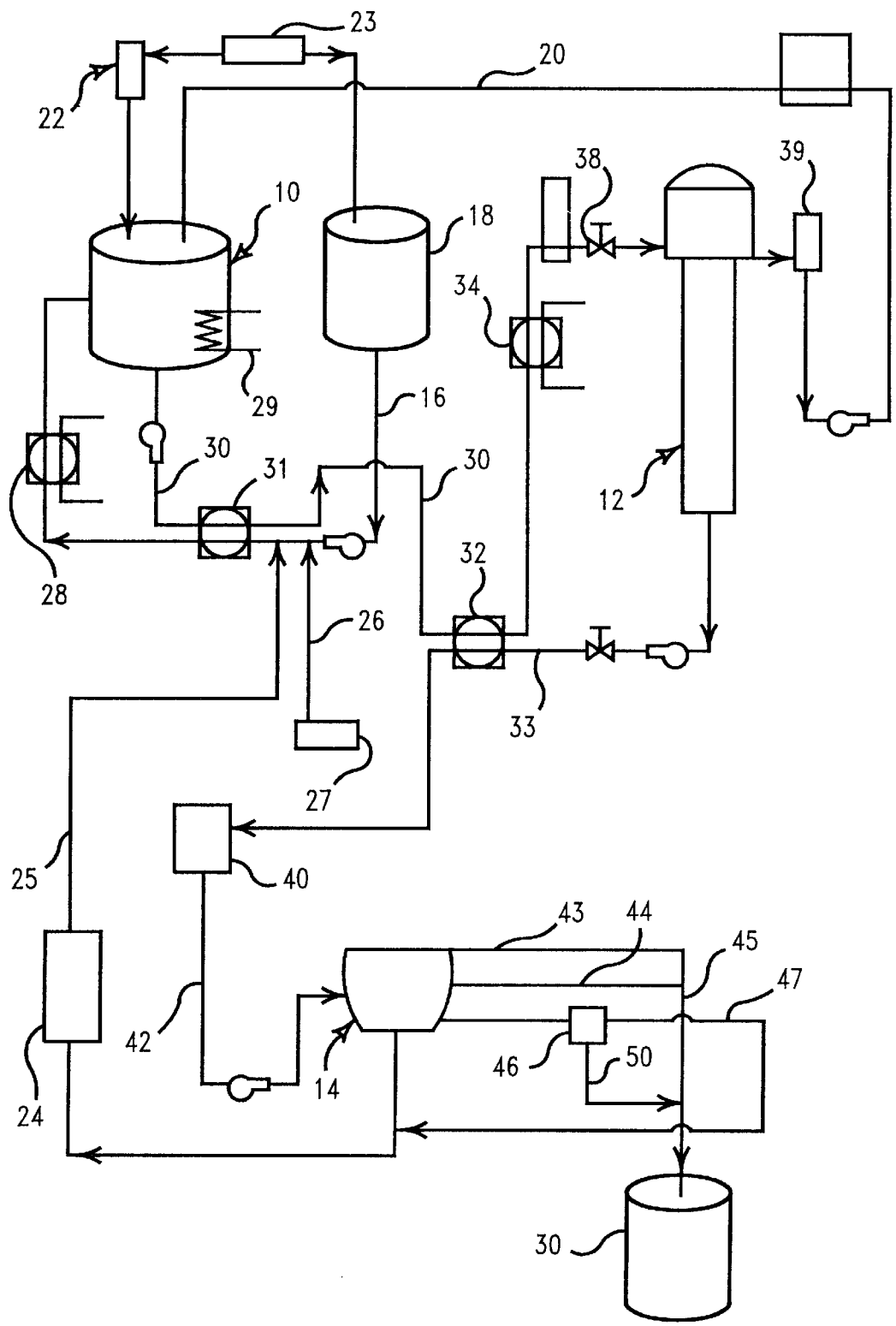

PROCESS FOR MAKING LOW CALORIE TRIGLYCERIDES HAVING LONG AND SHORT FATTY ACID CHAINS

FIELD OF THE INVENTION

The present invention relates to processes for making low calorie triglycerides.

BACKGROUND OF THE INVENTION

One of the most common metabolic problems among people today is obesity. This condition is due to a greater intake of calories than are expended. Fat is the most concentrated form of energy in the diet with each gram supplying approximately 9 calories. Overall, fat constitutes about 40 percent of the total calories in the diet. If the available calories from fat could be lowered without a decrease in the amount eaten, this would offer a very convenient and practical method by which obesity could be overcome.

Triglycerides are the main component of edible fats and constitute 90 percent of the total amount consumed. One method by which the caloric value of edible fat could be lowered would be to decrease the amount of triglyceride that is absorbed in the body. The usual edible triglyceride fats are almost completely absorbed. The absorbability of triglyceride fats can be decreased by altering the alcohol portion of the molecule. For example, U.S. Pat. No. 3,600,186 describes sugar or sugar alcohol fatty acid esters having at least 4 fatty acid ester groups have been used as nondigestible fats. U.S. Pat. No. 2,962,419 describes nondigestible esters formed by the reaction of a fatty acid with a polyol such as pentaerythritol. U.S. Pat. No. 4,582,715 describes alpha-acylated glycerides as nondigestible fats in low calorie fat-containing food compositions. Patent Cooperation Treaty (PCT) Application No. WO 93/00016 describes a low calorie fat substitute containing a sorbitol fatty acid ester.

Less digestible or absorbed fats have also been made by modification of the fatty acid portion of the ester. For example, U.S. Pat. No. 3,579,548 describes glycerol esters of alphabranched carboxylic acids. *J. Food Sci.*, Vol. 49 (1984), pp. 419–28, in an article by D. Hamm entitled, "Preparation and Evaluation of Trialkoxytricarballyate, Trialkoxycitrate, Trialkoxy-glycerolether, Jojoba Oil and Sucrose Polyester as Low Calorie Replacements of Edible Fats and Oils" describes the use of trialkoxycitrate or trialkoxytricarballyate as low calorie replacements of conventional edible fats and oils.

U.S. Pat. No. 4,959,466 describes partially esterified oligosaccharides and polysaccharides as indigestible fat substitutes. U.S. Pat. Nos. 4,927,658 and 4,927,659 describe trishydroxymethyl ethane and propane esterified with fatty acids or dicarboxylate-extended fatty acid derivatives as partially digestible synthetic fat replacements for foods.

A significant problem in attempting to formulate fat compounds having decreased absorbability and thus low calorie properties is to maintain the desirable and conventional physical properties of edible fat. To be practical, the low calorie fat must resemble conventional triglyceride fat and have the same utility in various fat-containing food compositions such as shortening, margarine and cake mixes. However, the combination of desirable fat-like properties with decreased absorbability or digestibility cannot be predicted with any degree of accuracy.

Food Technology at pg. 314, column 2, describes a process for preparing triglycerides by converting starting material fats to mono- and diglycerides by mixing with glycerol and sodium hydroxide for 0.3 to 3 hours at 200° C. to 250° C. The resulting technical grade mixture is acetylated.

U.S. Pat. No. 2,615,159 describes a process for preparing triglycerides by reacting triacetin with a conventional fat in the presence of a low temperature rearrangement catalyst such as sodium alkoxide suspended in xylene or other low boiling hydrocarbon which is miscible with the fats. The system has two phases.

U.S. Pat. No. 5,434,278 describes a solventless batch process for preparing triglycerides. The process involves interesterifying triglycerides bearing long $C_{16}$ to $C_{22}$ fatty acid chains with a mixture of triacetin and triglycerides bearing saturated $C_3$ to $C_{10}$ acid residues at a temperature of 100 to 150° C.

SUMMARY OF THE INVENTION

Accordingly, it is an object of the present invention to provide a process for making low calorie triglycerides.

It is another object of the present invention to provide a continuous process for making low calorie triglycerides.

It is also an object of the present invention to provide a process for making low calorie triglycerides which minimizes catalyst use and loss of starting materials.

It is a further object of the present invention to provide a process for making low calorie triglycerides exhibiting functionalities which may be used in a wide variety of products.

With regard to the foregoing and other objects, the present invention is directed to an improved process for making low calorie triglycerides. In general, the process comprises heating in a reactor a mixture comprising from about 1 to about 47 weight percent short triglycerides having $C_2$ to $C_{10}$ fatty acid chains and from about 53 to about 99 weight percent long triglycerides having $C_{10}$ to $C_{24}$ fatty acid chains in the presence of from about 0.01 to about 1.0 weight percent of an interesterification catalyst comprising a metal soap at a temperature of from about 200° C. to about 260° C. to produce a reaction product mixture containing unreacted short and long triglycerides, and low calorie triglycerides as an interesterification product of the short and long triglycerides comprising individual triglycerides having at least one long $C_{16}$ to $C_{24}$ fatty acid chain and at least one short $C_2$ to $C_{10}$ fatty acid chain wherein a substantial portion of the low calorie triglycerides have one long $C_{16}$ to $C_{24}$ fatty acid chain and two short $C_2$ to $C_{10}$ fatty acid chains. The low calorie triglycerides are separated from the reaction product mixture to isolate a low calorie triglyceride product.

The low calorie triglycerides are preferably separated from the reaction product mixture by a series of separations, the first of which comprises separating short triglycerides from the reaction product mixture by such means as a falling film evaporator employing a vacuum in the vapor space to promote evolution of the lower boiling short triglycerides and, thereafter, separating low calorie triglycerides from the remaining mixture by such means as a short path still.

According to one aspect of the invention, an improved process is provided for making low calorie triglycerides continuously. The process comprises heating in a reactor a mixture comprising from about 1 to about 47 weight percent short triglycerides having $C_2$ to $C_{10}$ fatty acid chains and from about 53 to about 99 weight percent long triglycerides having $C_{16}$ to $C_{24}$ fatty acid chains in the presence of from about 0.01 to about 1.0 weight percent of an interesterification catalyst comprising a metal soap at a temperature of from about 200° C. to about 260° C. to form a reaction product mixture containing unreacted short and long triglycerides, and low calorie triglycerides as an esterification product of the short and long triglycerides comprising individual triglycerides having at least one long $C_{16}$ to $C_{24}$ fatty acid chain and at least one short $C_2$ to $C_{10}$ fatty acid chain wherein a substantial portion of the low calorie triglycerides having one long $C_{16}$ to $C_{24}$ fatty acid chain and two short $C_2$ to $C_{10}$ fatty acid chains. The reaction product is heated in a first separation step at a temperature of from about 120° C. to about 250° C. and a pressure of from about 0.1 to about 10 mm Hg to produce vapor comprising short triglycerides and liquid comprising long triglycerides and low calorie triglycerides. The vapor is collected and condensed to provide a distillate which is recycled to the reactor. Liquid from the first separation step is heated in a second separation step at a temperature of from about 200° C. to about 270° C. and a pressure of from about 5 to about 200 microns to produce vapor comprising low calorie triglycerides and liquid comprising long triglycerides. The vapor is collected and condensed to provide a distillate containing low calorie triglycerides. Liquid from the second separation step is recycled to the reactor.

Low calorie triglycerides produced according to the invention are substantially free of contaminants and are characterized by low color, low odor and no taste. The low calorie triglycerides can be incorporated either alone or in combination with another fat or fat substitute into various food compositions. When practiced in accordance with a preferred embodiment on a continuous basis, the catalyst is recycled to the reactor with liquid from the second separation step which advantageously minimizes the cost of production.

It is also noted that the invention employs temperatures of up to about 260° C. for the interesterification reaction without decomposition or darkening of the low calorie triglycerides. This is unexpected since the prior art suggests interesterification reactions for triglycerides at temperatures no greater than about 150° C. However, low calorie triglycerides produced by the process of the invention do not exhibit the undesirable properties of previous interesterified triglycerides produced at relatively high temperatures.

BRIEF DESCRIPTION OF THE DRAWING

The above and other aspects and advantages of the invention will now be further described in the following detailed description considered in conjunction with the drawing which is a diagrammatic illustration depicting steps of a preferred embodiment of a continuous process for preparing low calorie triglycerides in accordance with the invention.

DESCRIPTION OF THE DRAWING

The invention provides a process for making low calorie triglycerides. The process involves interesterifying at least one short triglyceride having $C_2$ to $C_{10}$ fatty acid chains with at least one long triglyceride having $C_{16}$ to $C_{24}$ fatty acid chains in the presence of a catalyst and without a solvent for such time and under such conditions that low calorie triglycerides are formed in a reaction product containing unreacted short and long triglycerides. The low calorie triglycerides are the interesterification product of the long and short triglycerides and comprise individual triglycerides having at least one long $C1_6$ to $C_{24}$ fatty acid chain and at least one short $C_2$ to $C_{10}$ fatty acid chain. Preferably the low calorie triglyceride product contains a substantial portion (at least about 50 percent by weight, preferably above 80 percent by weight, and most preferably above 90 percent by weight) of low calorie triglycerides have one long $C_{16}$ to $C_{24}$ fatty acid chain and two short $C_2$ to $C_{10}$ fatty acid chains.

As used herein, "interesterification" means a reaction of triacylglycerol structures whereby individual positions of esterified fatty acids are interchanged on the glycerol moiety.

As used herein, "solvent" means a material which is liquid at the reaction temperature and pressure and will dissolve, suspend or hold fatty acids in the reaction to promote intimate contact of the reactants and catalyst for the desired interesterification substantially without taking part or being consumed in the interesterification reaction.

The long triglycerides for the reaction may be obtained from natural oils such as soybean, safflower, sunflower, sesame, peanut, corn, olive, rice bran, mustard seed, cottonseed, poppyseed, rapeseed, marine, meadowfoam and the like oils; fats such as palm oil, tallow, lard, and shea butter; or plant waxes such as jojoba. Fat mixtures and/or fractions, crystallized fats, interesterified fats and mixtures of these may also be employed, as can synthetic fats such as tristearin and palmitostearin. Preferably, the long triglycerides have $C_{18}$ to $C_{22}$ fatty acid chains. Particularly preferred sources of long triglycerides are soybean oil, cottonseed oil and sunflower oil. The long triglycerides may be hydrogenated before or after the interesterification reaction.

The long triglycerides can therefore be derived from non-hydrogenated, partially hydrogenated or fully hydrogenated oils, fats or waxes. Hydrogenated fats having at least about 70 percent stearic acid chains such as hydrogenated peanut oil, hydrogenated olive oil, hydrogenated soybean oil, hydrogenated sesame oil, and hydrogenated corn oil are especially desirable for some embodiments. Other embodiments may employ hydrogenated fats having at least about 90 percent stearic acid chains such as hydrogenated sunflower oil, hydrogenated safflower oil and hydrogenated canola. A mixture of hydrogenated fats may be employed. Using fully hydrogenated feedstocks is advantageous because they yield products low in trans unsaturation. It is noted that the oils, fats, or waxes may be hydrogenated before or after incorporation into the low calorie triglycerides of this invention.

Saturated $C_{16}$ to $C_{24}$ fatty acid chains in the long triglycerides include, but are not limited to, palmitic (hexadecanoic), stearic (octadecanoic), arachidic (eicoisanoic), behenic (docosanoic), and the like. The fatty acid chains may also be derived by hydrogenating fats or oils containing unsaturated acids such as, for example, palmitoleic (9hexadecanoic), oleic (cis-9-octadecenoic), elaidic (trans-9-octadecenoic), vaccenic (trans-11-octadecenoic), linoleic (cis, cis-9-12-octadecadienoic), linolenic (9,12,15-octadecatrienoic and 6,9,12-octadecatrienoic), eleostearic (9,11,13-octadecatrienoic), arachidonic (5,8,11,14-eicosatetraenoic), and the like. Chemical names include isomeric variations.

The short triglycerides for the reaction may be triglycerides bearing acetic, propionic, butyric, caproic, caprylic, pelargoinic and/or capric short or medium acid chain lengths such as, for example, triacetin, tripropionin, tributyrin, tricaproin, tricaprylin, tripelargonin and tricaprin, and any mixtures or combinations of these. Mixtures of short triglycerides may be employed. Preferably, the short triglycerides have $C_2$ to $C_4$ fatty acid chains. The short triglycerides may be either saturated or unsaturated, straight or branched. As used herein, chemical names include isomeric variations.

For example, "butyric acid" includes normal-butyric acid (butanoic) and iso-butyric (2-methylpropanoic) acid, "valeric acid" includes normal-valeric (pentanoic) and iso-valeric (3-methylbutanoic), and so forth. Preferred short triglycerides are triacetin, tripropionin and tributyrin.

It is within the scope of this invention to alter the fatty acid portion of the short and/or long triglycerides with a sugar fatty acid ester. The fatty acid portion of the short and/or long triglycerides may also be modified with trishydroxymethyl alkane ester derivatives such as fatty acid and dicarboxylate-extended fatty acid esters of monomeric and dimeric trishydroxymethyl alkane as partially digestible edible fat replacements.

The interesterification catalyst is preferably a metal soap. The metal soap is a reaction product of a fatty acid ester and an alkali metal. Suitable alkali metals include lithium, sodium, potassium, calcium, rubidium, cesium or a mixture or alloy of these. Examples of metal soap catalysts include potassium stearate, calcium stearate, aluminum acetate, copper acetate, and sodium stearate. Combinations of interesterification catalysts may also be used. Preferably, the interesterification catalyst is potassium stearate and aluminum acetate. The metal soap catalyst used herein is preferably a relatively weak as opposed to a strong base catalyst which is typically used as an interesterification catalyst.

The interesterification catalyst is added in an amount of from about 0.01 to about 1.0 weight percent, preferably from about 0.1 to about 0.5 weight percent, and most preferably from about 0.2 to about 0.3 weight percent based on the weight of starting materials. The interesterification catalyst may be added in the form of a slurry in the short triglycerides.

In one embodiment triacetin, tripropionin and a long triglyceride having $C_{16}$ to $C_{24}$ fatty acid chains such as soybean oil are employed. Another embodiment employs tributyrin and a long triglyceride having $C_{16}$ to $C_{24}$ fatty acid chains. A third embodiment employs triacetin and a long triglyceride having $C_{16}$ to $C_{24}$ fatty acid chains.

The first step of the process comprises heating in a reactor a mixture containing from about 1 to about 47 weight percent short triglycerides having $C_2$ to $C_{10}$ fatty acid chains and from about 53 to about 99 weight percent long triglycerides having $C_{16}$ to $C_{24}$ fatty acid chains in the presence of from about 0.01 to about 1.0 weight percent of an interesterification catalyst to produce a reaction product mixture containing unreacted short and long triglycerides and low calorie triglycerides as an interesterification product of the long and short triglycerides. Preferably, the mixture comprises 40 to 47 weight percent short triglycerides, 53 to 60 weight percent long triglycerides and 0.1 to 0.5 weight percent interesterification catalyst.

The reaction is conducted at a temperature of from about 200° C. to about 260° C. and a pressure of from about atmospheric to a pressure above atmospheric for from about 1 to about 10 hours. Preferably, the reaction is conducted at a temperature of from about 240° C. to about 250° C., a pressure of slightly above atmospheric and a reaction time of from about 2 to about 4 hours. It is noted that a pressure less than atmospheric may result in removal of short triglycerides which is undesirable in the reaction step of the process. A nitrogen purge is preferably used in the reactor to limit oxidation of the materials and is principally responsible for the slightly elevated pressure.

The reaction is preferably continued until achieving a conversion to low calorie triglycerides in the reaction product mixture in the range of from about 50 to about 60 percent by weight based on the weight of the starting materials. The reaction product mixture is then treated to separate unreacted long and short triglycerides from the desired low calorie triglycerides. Preferably, the separation is carried out in two steps which may be conducted in a single or multiple separation units.

In the first separation step, unreacted short triglycerides are separated from the reaction product mixture. The separation may be carried out by any separation method known to those skilled in the art such as crystallization, supercritical extraction, evaporation or distillation. Preferably, the first separation is carried out at an elevated temperature and reduced pressure to drive off the short triglycerides as vapor.

In a preferred embodiment, the first separation is carried out using either a short path still, a centrifugal molecular still, a high vacuum wiped film evaporator or a falling film evaporator. Most preferably, the first separation step is carried out using a falling film evaporator which employs a vacuum in the vapor space to promote evolution of the lower boiling short triglycerides. The short triglycerides are vaporized from the reaction product by heating the reaction product at a temperature of from about 120° C. to about 250° C. with the vapor space maintained at a pressure of from about 0.1 to about 10 mm Hg. Preferably, the reaction product is heated in the unit at a temperature of from about 160° C. to about 225° C. and vapor containing the short triglycerides flashes from the liquid into the vapor space of the vessel at a pressure of from about 0.5 to about 1.5 mm Hg. The temperature to which the material is heated may vary depending on the vacuum employed. The vaporized short triglycerides are collected, condensed and in the continuous process are preferably recycled to the reactor.

After separation of the short triglycerides, the remaining reaction product mixture in liquid form is treated in a second separation step to separate low calorie triglycerides from unreacted long triglycerides and any short triglycerides that remain after the first separation step. The second separation may be carried out by any separation method known to those skilled in the art such as crystallization, supercritical extraction, evaporation and distillation. Preferably, the second separation is carried out at an elevated temperature and reduced pressure to remove low calorie triglycerides from the product mixture as vapor.

In a preferred embodiment, the second separation step is carried out using either a short path still, a centrifugal molecular still, or a high vacuum wiped film evaporator. Most preferably, the second separation step is carried out using a short path still having at least two separate collection and condensation points for vapors. The temperature employed in the evaporator preferably ranges from about 200° C. to about 270° C. and the pressure is preferably from about 5 to about 200 microns. Most preferably, the separation is conducted at a temperature of from about 225° C. to about 240° C. and a pressure of from about 10 to about 50 microns. The low calorie triglycerides which are evolved as vapor are collected, condensed and conducted to storage as product. Long triglycerides which remain as liquid after low calorie triglycerides are vaporized may be recycled to the reactor.

According to the process of the present invention, the yield of the low calorie triglyceride product with recycle is greater than 90 percent, preferably greater than 95 percent and most preferably greater than 98 percent. As used herein, "yield" for the continuous process means the weight of the low calorie triglyceride product produced per unit of time divided by the weight of the long and short triglycerides supplied to the reactor over that period of time less the proportion of the long and short triglycerides provided by recycle. No significant solidification or precipitation of the reactants or product have been observed in the process.

The long and short triglycerides for producing the low calorie triglycerides are selected to provide a discernible fatty character. An advantage of the process of the present invention is that functional properties can be tailored by the selection of short and long triglyceride groups. For example, formulations for chocolate or confectionery applications can employ groups or components yielding sharply melting mixtures, salad oils can employ groups yielding medium melting mixtures that do not readily crystallize upon refrigeration, margarines and shortenings can employ groups stable to oxidation on storage, and so forth.

The low calorie triglycerides of this invention may be incorporated either alone or in combination with another fat and/or fat substitute or mimetic, into any food composition, or used in conjunction with any edible material. Other fats include natural triglycerides rich in highly desirable or essential fatty acids such as oleic, linoleic, nolenic, or eicoaspeniaenoic acid, triglyceride bearing fatty acids having beneficial attributes such as those associated with conjugated linoleic acid isomers, medium chain triglycerides and the like. Other fat mimetic include, but are not limited to, sugar esters, neoalkyl ester, polyglycerol esters, malonate esters, propoxylated glycerols, retrofats, carboxy/carboxylates, polyvinyl alcohol esters and the like. When employed either alone or in products with other fats, the low calorie triglycerides are desirably added in amounts effective to provide a significant calorie reduction of the calories due to fat. For example, a 10 percent or greater replacement would be effective for this purpose, and replacements of at least 25 percent, more particularly 50 to 100 percent, are desired in many cases.

As used herein, "edible material" means anything edible, whether or not intended for nutrition, e.g., it can be an additive such as an antioxidant for fats or oils, an antispatter agent, an emulsifier, a texture modifier such as a plasticizer for chewing gum, a component for cosmetics, or other minor functional ingredient such as a carrier or diluent for use in flavorings, pharmaceuticals, and the like.

The low calorie triglycerides of this invention can be employed as fat replacements in fat-containing edible emulsions comprising an oil phase and an aqueous phase, including those high in fat, such as margarines and salad dressings, and those high in water, such as low fat spreads. The triglycerides of this invention can be employed as full or partial fat substitutes in dairy, meat, nut, egg, and other food products having a high natural fat component, and in vegetable, cereal and other products having a low natural fat component. The triglycerides can be employed as ingredients for all types of leavened baked products and unleavened baked products, and as coatings or coating ingredients for the same types of products. The triglycerides can be employed as a ingredient or a coating for snack food products, as well as a frying oil or a frying oil ingredient for fried snacks. In addition, the low calorie triglycerides can be employed to form edible barrier layers, either on the exposed surfaces of foods or as internal barrier layers used to separate various portions of a food product, e.g., in frozen pizza, nut coatings, or as a barrier between a dessert filling and an outer edible shell in fruit filled cookies and the like.

Representative fat-containing food products which can contain, in addition to other food ingredients, the low calorie triglycerides of this invention in full or partial replacement of natural or synthetic fat are frozen desserts, e.g. frozen novelties, ice cream, sherbet, ices, and milk shakes; salad dressings; mayonnaises and mustards; dairy and non-dairy cheese spreads; margarine, margarine substitutes and blends; flavored dips; flavored bread or biscuit spreads; filled dairy products such as filled cream and filled milk; frying fats and oils; cocoa butter replacements and blends; candy, especially fatty candies such as those containing peanut butter or chocolate; reformed and comminuted meats; meat substitutes and extenders; egg products and substitutes; nut products such as peanut butter, vegetable and fruit products; pet foods; whipped toppings; compound coatings; coffee lighteners, liquid and dried; puddings and pie fillings; frostings and fillings; chewing gum; breakfast cereals; bakery products, e.g., cakes, breads, rolls, pastries, cookies, biscuits, and savory crackers; and mixes or ingredient premixes for any of these. The low calorie triglycerides of this invention may also be employed in any flavor, nutrient, drug or functional additive delivery system.

An advantage of the invention is that the low calorie triglycerides perform the following functions in foods and food processing: alpha crystalline stabilization, lubrication, plasticizing, softening, defoaming, antidusting and film forming. The low calorie triglycerides may also act as solvents or plasticizers for certain plastic wrappers such as polyethylene, polyamides, polystyrene and polyvinyl chloride.

Referring to the drawing, there is shown a process flow diagram for a preferred embodiment of a continuous process according to the invention employing a recycle system for supply of long and short triglycerides for the interesterification reaction along with the initial charge and make-up of reactants. The process comprises three principal unit operations, the first being an interesterification of long and short triglycerides using a continuous stirred tank reactor (CSTR) 10, the second being evaporation of unreacted short triglycerides from the reaction mixture using a falling film evaporator 12, and the third being a multi-component separation using a short path still 14 for separating the low calorie product from unreacted long and short triglycerides carried over from the first separation operation.

Short triglycerides are supplied to the CSTR 10 by means of a conduit 16 from tank 18 and via recycle conduit 20 from falling film evaporator 12. Catalyst is supplied to CSTR 10 from mix tank 22 slurried with fresh short triglycerides delivered to tank 22 via conduit 26 leading from short triglyceride source 23 which also supplies fresh or make-up short triglycerides to tank 18.

Long triglycerides are supplied to CSTR 10 via recycle conduit 25 (with interposed surge tank 24) from short path still 14 which merges the flow of recycled long triglycerides with short triglycerides supplied to CSTR 10 in conduit 16. Fresh or make-up long triglycerides are supplied to CSTR 10 via conduit 26 connected in flow communication with conduit 16 from a source of long triglycerides 27. The stream of reactants delivered to CSTR 10 is preheated in heat exchanger 28.

The reaction mixture in CSTR 10 is preferably heated indirectly by hot oil circulating in coils 29, and the contents are sealed under a nitrogen blanket supplied from a suitable source (not shown). CSTR 10 is operated to provide a residence time of the reactants in the neighborhood of from about 1 to about 10 hours by appropriate sizing of the tank and placement of the inlet and outlet conduit according to well-known chemical engineering principles.

Reaction product from CSTR 10 flows through conduit 30 to falling film evaporator 12 after initially exchanging heat with incoming long and short triglycerides in conduit 16 using heat exchanger 31. Product mixture in conduit 30, after losing heat to reactant stream flowing in conduit 16 via heat exchanger 31, is reheated before delivery into falling film evaporator 12 by heat exchanger 32 wherein heat energy in liquid flowing from falling film evaporator 12 in conduit 33 is transferred to the product mixture. Further heating of the product mixture flowing in conduit 30 is achieved using heat exchanger 34. Heat exchanger 34 brings the product mixture flowing in conduit 34 to from about 140° C. to about 225° C. and the mixture is released into falling film evaporator 12 across orifice 38. Vaporized unreacted short triglycerides are collected and condensed in condenser 39 and the resulting distillate is recycled to CSTR 10 by means of conduit 20. Liquid residue from falling film evaporator 12 containing principally unreacted long and low calorie triglycerides with a minor amount of short triglycerides flows to a ballast tank 40 via conduit 33 after exchanging heat in heat exchanger 32 with reaction product mixture flowing in conduit 30.

From ballast tank 40, the liquid is conducted via conduit 42 to short path still 14 where low calorie triglycerides and a small amount of short triglycerides are vaporized from the liquid and are collected, condensed and passed as distillate to storage tank 30 via conduits 43 and 44 which merge into product conduit 45 leading to tank 30. Unreacted long triglycerides are recycled as liquid from short path still 14 to CSTR 10 via conduit 25.

A portion of the vapors collected and condensed as the lightest or lowest boiling portion of the vapors in short path still 14 are flash distilled in unit 46 to vaporize and remove a substantial portion of any short triglycerides carried into short path still 14 from falling film evaporator 12, which are collected, condensed and recycled to CSTR 10 as distillate via conduit 47 which merges into long triglycerides recycle conduit 25. Liquid from unit 46 containing principally low calorie triglyceride product is delivered to tank 30 via conduit 50 which merges into product conduit 45.

With regard to the above-described continuous process, it is noted that the process achieves a relatively high yield and an economical mode of operation with improved product quality. One advantage of the process is that catalyst employed in CSTR 10 passes through the separation steps with the liquid or non-vaporized streams and is recycled to CSTR 10 with unreacted long triglycerides in conduit 25. Accordingly, substantially all of the unreacted long and short triglycerides are recycled which promotes economics in reactant costs and the catalyst is substantially conserved so that the catalyst expense component of the product cost is significantly reduced. The recycle also enables improved economy and control in terms of mixing fresh and recycled long and short triglycerides so that the properties of the low calorie triglycerides can be tailored by adjustment of the relative proportions and qualities of long and short triglycerides supplied to CSTR 10. The recycle and the overall arrangement of process steps promotes energy conservation by enabling exchange of heat energy between and among the various streams conveyed from operation to operation.

The process of the invention employs various conventional pumps and controls for conducting the flow of material at appropriate rates between the various unit operations. For the purpose of clarity, the details and placement of such pumps and controls have been omitted, it being understood that the person of ordinary skill in the art can readily adapt necessary pumps, valves and various controls etc., for the practice of the process.

The following nonlimiting examples illustrate further aspects of the invention.

EXAMPLE 1

A continuous stirred tank reactor equipped with a mechanical agitator, addition pipelines, thermowell, heating coils, and nitrogen atmosphere was charged with fresh triacetin, recycled triacetin, fresh tripropionin, recycled tripropionin, fresh hydrogenated soybean oil, recycled long triglycerides, and a catalyst system consisting of 0.15 weight percent potassium stearate and 0.1 weight percent aluminum acetate. The reaction was maintained by constant mixing and heating. A gas-fired hot oil system maintained a reaction temperature of 235° C. The average reactor residence time was about 2.4 hours.

The reaction product mixture was comprised of 38 weight percent unreacted short triglycerides comprising triacetin, tripropionin and combinations thereof, 12 weight percent unreacted long triglycerides comprising 90 percent stearic acid and 10 percent palmitic acid, and 50 weight percent low calorie triglyceride product comprising 30 percent of a triglyceride having one long fatty acid chain and two short fatty acid chains (monolong) and 20 percent of a triglyceride having two long fatty acid chains and one short fatty acid chain (dilong). The reaction product mixture was fed to a falling film evaporator operated at a temperature of 185° C. and about 0.8 mm Hg to remove unreacted short triglycerides.

The underflow from the falling film evaporator was fed to a centrifugal molecular still operated at 224° C. at 40 microns to distill a low calorie triglyceride product from the underflow. The low calorie triglyceride product was comprised of 0.1 weight percent short triglycerides, 0.1 weight percent long triglycerides, 88.1 weight percent monolong and 11.7 weight percent dilong.

EXAMPLE 2

A continuous stirred tank reactor equipped with a mechanical agitator, addition pipelines, thermowell, heating coils, and nitrogen atmosphere was charged with fresh tributyrin, recycled tributyrin, fresh hydrogenated soybean oil, recycled long triglycerides, and a catalyst system consisting of 0.15 weight percent potassium stearate and 0.1 weight percent aluminum acetate. The reaction was maintained by constant mixing and heating. A gas-fired hot oil system maintained a reaction temperature of 250° C. The average reactor residence time was about 2.5 hours.

The reaction product mixture was comprised of 23.4 weight percent tributyrin, 18.2 weight percent unreacted long triglycerides comprising 90 percent stearic acid and 10 percent palmitic acid, and 58.4 weight percent low calorie triglyceride product comprising 25.6 percent of monolong and 32.8 percent of dilong. The reaction product mixture was fed to a falling film evaporator operated at a temperature of 225° C. and 1.2 mm Hg to remove unreacted tributyrin.

The underflow from the falling film evaporator was fed to a centrifugal molecular still operated at 219° C. and 11 to 39 microns to distill a low calorie triglyceride product from the underflow. The low calorie triglyceride product was comprised of 0.1 weight percent short triglycerides, 0.1 weight percent long triglycerides, 93.9 weight percent monolong and 5.9 weight percent dilong.

EXAMPLE 3

A continuous stirred tank reactor equipped with a mechanical agitator, addition pipelines, thermowell, heating coils, and nitrogen atmosphere was charged with fresh triacetin, recycled triacetin, fresh partially hydrogenated soybean oil, recycled long triglycerides, and a catalyst system consisting of 0.15 weight percent potassium stearate and 0.1 weight percent aluminum acetate. The reaction was maintained by constant mixing and heating. A reaction temperature of 237° C. was maintained. The average reactor residence time was about 1.4 hours.

The reaction product mixture was comprised of 23.4 weight percent triacetin, 27.3 weight percent soybean oil, and 49.3 weight percent low calorie triglyceride product comprising 28.3 percent of monolong and 21.0 percent of dilong. The reaction product mixture was fed to a centrifugal molecular still operated at a temperature of 137° C. and 109 microns to remove unreacted triacetin.

The underflow from the centrifugal molecular still was fed to a second centrifugal molecular still operated at 219° C. and 12 microns to distill a low calorie triglyceride product from the underflow. The low calorie triglyceride product was comprised of 0.03 weight percent short triglycerides, 0.0 weight percent long triglycerides, 92.6 weight percent monolong and 7.3 weight percent dilong.

While the invention has been described with particular reference to certain embodiments thereof, it will be understood that changes and modifications may be made which are within the skill of the art. The present invention is limited only by the claims that follow.

What is claimed is:

1. A process for making low calorie triglycerides which comprises heating in a reactor a mixture comprising from about 1 to about 47 weight percent short triglycerides having $C_2$ to $C_{10}$ fatty acid chains and from about 53 to about 99 weight percent long triglycerides having $C_{16}$ to $C_{24}$ fatty acid chains in the presence of from about 0.01 to about 1.0 weight percent of an interesterification catalyst comprising a metal soap at a temperature of from about 200° C. to about 260° C. to produce a reaction product mixture containing unreacted short and long triglycerides and low calorie triglycerides as an interesterification product of the long and short triglycerides comprising individual triglycerides having at least one long $C_{16}$ to $C_{24}$ fatty acid chain and at least one short $C_2$ to $C_{10}$ fatty acid chain wherein at least a substantial portion of the triglyceride have one long $C_{16}$ to $C_{24}$ fatty acid chain and two short $C_2$ to $C_{10}$ fatty acid chains, and separating at least a substantial portion of the low calorie triglycerides from the reaction product mixture.

2. The process of claim 1 wherein the low calorie triglycerides comprise triglyceride having one long $C_{16}$ to $C_{24}$ fatty acid chain and two short $C_2$ to $C_{10}$ fatty acid chains.

3. A continuous process for making low calorie triglycerides which comprises heating in a reactor a mixture comprising from about 1 to about 47 weight percent short triglycerides having $C_2$ to $C_{10}$ fatty acid chains and from about 53 to about 99 weight percent long triglycerides having $C_{16}$ to $C_{24}$ fatty acid chains in the presence of from about 0.01 to about 1.0 weight percent of an interesterification catalyst comprising a metal soap at a temperature of from about 200° C. to about 260° C. to produce a reaction product mixture containing unreacted short and long triglycerides and low calorie triglycerides as an interesterification product of the long and short triglycerides comprising individual triglycerides having at least one long $C_{16}$ to $C_{24}$ fatty acid chain and at least one short $C_2$ to $C_{10}$ fatty acid chain wherein at least a substantial portion of the low calorie triglycerides are triglycerides having one long $C_{16}$ to $C_{24}$ fatty acid chin and two short $C_2$ to $C_{10}$ fatty acid chains; heating the reaction product mixture in a first separation step at a temperature of from about 120° C. to about 250° C. and a pressure of from about 0.1 to about 10 mm Hg to produce vapor comprising unreacted short triglycerides and liquid comprising unreacted long triglycerides and low calorie triglycerides; collecting and condensing vapor from the first separation step as distillate and recycling the distillate to the reactor; heating liquid from the first separation in a second separation step at a temperature of from about 200° C. to about 270° C. and a pressure of from about 5 to about 200 microns to produce vapor comprising low calorie triglycerides and liquid comprising unreacted long triglycerides; collecting and condensing vapor from the second separation step as distillate containing low calorie triglycerides; and recycling liquid from the second separation step to the reactor.

4. The process of claim 1 wherein the long triglycerides are selected from the group consisting of natural oils, fats and plant waxes.

5. The process of claim 4 wherein the natural oil is selected from the group consisting of soybean, safflower, sunflower, sesame, peanut, corn, olive, rice bran, mustard seed, cottonseed, poppyseed, rapeseed, marine, meadowfoam and combinations thereof.

6. The process of claim 4 wherein the fat is selected from the group consisting of palm oil, tallow, lard, and shea butter.

7. The process of claim 4 wherein the plant wax is jojoba.

8. The process of claim 1 wherein the long triglycerides are fully hydrogenated.

9. The process of claim 1 wherein the short triglycerides are selected from the group consisting of triacetin, tripropionin, tributyrin, tricaproin, tricaprylin, tripelargonin, tricaprin and combinations thereof.

10. The process of claim 1 wherein the catalyst is selected from the group consisting of potassium stearate, calcium stearate, aluminum acetate, copper acetate, sodium stearate and combinations thereof.

11. The process of claim 10 wherein the catalyst is hydrated dibasic aluminum acetate and potassium stearate.

12. The process of claim 1 wherein the catalyst is present in an amount of from about 0.1 to about 0.5 weight percent.

13. The process of claim 12 wherein the catalyst is present in an amount of from about 0.2 to about 0.3 weight percent.

14. The process of claim 3 wherein the separations are carried out in one unit.

15. The process of claim 1 wherein the reaction mixture is heated at a temperature of from about 240° C. to about 250° C. and a pressure of about atmospheric for from about 1 to about 10 hours.

16. The process of claim 3 wherein the first separation is conducted at a temperature of from about 165° C. to about 225° C. and a pressure of from about 0.5 to about 1.5 mm Hg.

17. The process of claim 3 wherein the first separation is carried out in an apparatus selected from the group consisting of a short path still, a centrifugal molecular still, a high vacuum wiped film evaporator and a falling film evaporator.

18. The process of claim 17 wherein the falling film evaporator employs a vacuum in the vapor space.

19. The process of claim 3 wherein the second separation is conducted at a temperature of from about 225° C. to about 240° C. and a pressure of from about 10 to about 50 microns.

20. The process of claim 3 wherein the second separation is carried out in an apparatus selected from the group consisting of a short path still, a centrifugal molecular still, and a high vacuum wiped film evaporator.

21. The process of claim 20 wherein the short path still has at least two separate collection and condensation points for vapors.

22. The process of claim 21 wherein the short path still has three separate collection and condensation points for vapors.

* * * * *